(12) United States Patent
Liu (10) Patent No.: US 10,556,127 B2
(45) Date of Patent: Feb. 11, 2020

(54) NEUTRON THERAPY APPARATUS

(71) Applicant: NEUBORON MEDTECH LTD., Nanjing, Jiangsu (CN)

(72) Inventor: Yuanhao Liu, Jiangsu (CN)

(73) Assignee: NEUBORON MEDTECH LTD., Nanjing, Jiangsu Province (CN)

( * ) Notice: Subject to any disclaimer, the term of this patent is extended or adjusted under 35 U.S.C. 154(b) by 0 days.

(21) Appl. No.: 16/212,995

(22) Filed: Dec. 7, 2018

(65) Prior Publication Data

US 2019/0105512 A1 Apr. 11, 2019

Related U.S. Application Data

(63) Continuation of application No. PCT/CN2016/110396, filed on Dec. 16, 2016.

(30) Foreign Application Priority Data

Jul. 4, 2016 (CN) .......................... 2016 1 0517978
Jul. 4, 2016 (CN) ..................... 2016 2 0699033 U (51) Int. Cl.
*A61N 5/10* (2006.01)
*G21K 5/00* (2006.01)

(52) U.S. Cl.
CPC ............. *A61N 5/1042* (2013.01); *A61N 5/10* (2013.01); *A61N 5/1081* (2013.01);
(Continued)

(58) Field of Classification Search
CPC ...... A61N 5/10; A61N 5/1081; A61N 5/1082; A61N 5/1083; A61N 2005/109; G21K 1/02

See application file for complete search history.

(56) References Cited

U.S. PATENT DOCUMENTS 3,925,676 A * 12/1975 Bigham .................. A61N 5/10
376/112
4,112,306 A * 9/1978 Nunan ..................... A61N 5/10
315/502
(Continued)

FOREIGN PATENT DOCUMENTS

CN 101829409 A 9/2010
CN 104221093 A 12/2014
(Continued)

OTHER PUBLICATIONS

International Search Report of PCT/CN2016/110396, dated Mar. 22, 2017.

*Primary Examiner* — Wyatt A Stoffa
(74) *Attorney, Agent, or Firm* — Locke Lord LLP; Tim Tingkang Xia, Esq.

(57) ABSTRACT

In order to provide a neutron therapy apparatus which give multi angles neutron beam irradiation, the neutron therapy apparatus includes: a beam shaping assembly including a moderator and a reflector surrounding the moderator, wherein the moderator moderates neutrons to a predetermined energy spectrum and the reflector guides deflected neutrons back to enhance the neutron intensity in the predetermined energy spectrum; a neutron generator embedded inside the beam shaping assembly, wherein the neutron generator generates neutrons after irradiated by an ion beam; at least a tube for transmitting the ion beam to the neutron generator, wherein the tube defines at least an axis; deflection magnets for changing the transmission direction of the ion beam; a collimator for concentrating neutrons; and an irradiation room for receiving a irradiated object, wherein the beam shaping assembly rotates around the axis of the tube.

15 Claims, 8 Drawing Sheets

(52) U.S. Cl.
CPC ............ *A61N 5/1082* (2013.01); *G21K 5/00* (2013.01); *A61N 2005/109* (2013.01); *A61N 2005/1087* (2013.01); *A61N 2005/1094* (2013.01); *A61N 2005/1095* (2013.01)

(56) References Cited

U.S. PATENT DOCUMENTS

| | | | |
|---|---|---|---|
| 5,920,601 | A | 7/1999 | Nigg et al. |
| 8,779,393 | B2 * | 7/2014 | Sasai .................... A61N 5/1081 250/396 R |
| 9,789,340 | B2 * | 10/2017 | Liu ..................... A61N 5/1077 |
| 10,082,587 | B1 * | 9/2018 | Akabori .................... G01T 7/00 |
| 10,155,123 | B2 * | 12/2018 | Mukawa ................. A61N 5/10 |
| 2013/0066135 | A1 | 3/2013 | Rosa et al. |
| 2015/0105604 | A1 * | 4/2015 | Liu ..................... A61N 5/1077 600/1 |
| 2015/0216029 | A1 * | 7/2015 | Tsuchida ................. H05H 6/00 376/151 |
| 2018/0160521 | A1 * | 6/2018 | Hsueh Liu ............... H05H 6/00 |
| 2019/0030369 | A1 * | 1/2019 | Mukawa ............. A61N 5/1031 |

FOREIGN PATENT DOCUMENTS

| | | | | |
|---|---|---|---|---|
| CN | 104941075 | A | | 9/2015 |
| JP | 2008022920 | A | | 2/2008 |
| JP | 2009189643 | A | * | 8/2009 ........... A61N 5/1081 |
| JP | 2014115122 | A | | 6/2014 |
| WO | 2018006550 | A1 | | 1/2018 |

* cited by examiner

NEUTRON THERAPY APPARATUS

RELATED APPLICATION INFORMATION

This application is a continuation of International Application No. PCT/CN2016/110396, filed on Dec. 16, 2016, which claims priority to Chinese Patent Application No. 201610517978.4, filed on Jul. 4, 2016; Chinese Patent Application No. 201620699033.4, filed on Jul. 4, 2016, the disclosures of which are hereby incorporated by reference.

FIELD OF THE DISCLOSURE

The present disclosure relates to an irradiation apparatus for radioactive rays, especially to a neutron therapy apparatus.

BACKGROUND OF THE DISCLOSURE

A neutron therapy apparatus used in boron neutron capture therapy apparatus normally gives the irradiated object multiple angles irradiation because of need. In the past, in order to achieve this kind of multiple angles irradiation, the neutron therapy apparatus was normally fixed on some rotary apparatus which had enormous structure, and the rotation of the neutron therapy apparatus was driven by the rotation of the rotary apparatus. Obviously, the structure of the neutron therapy apparatus itself is already quite big, so it may need a rotary apparatus even bigger than the neutron therapy apparatus to drive the rotation of the neutron therapy apparatus by an external rotary apparatus, and quite large space is further needed to satisfy the rotation of the neutron therapy apparatus and the rotary apparatus at the same time. Therefore the whole apparatus is not only bulky but also with low application, and it is not benefit to the miniaturization design of the neutron therapy apparatus.

The statements in this section merely provide background information related to the present disclosure and may not constitute prior art.

SUMMARY

In order to provide a neutron therapy apparatus which give multi angles neutron beam irradiation, in one aspect of the present disclosure provides a neutron therapy apparatus includes: a beam shaping assembly including a moderator and a reflector surrounding the moderator, wherein the moderator moderates neutrons to a predetermined energy spectrum and the reflector guides deflected neutrons back to enhance the neutron intensity in the predetermined energy spectrum; a neutron generator embedded inside the beam shaping assembly, wherein the neutron generator generates neutrons after irradiated by an ion beam; at least a tube for transmitting the ion beam to the neutron generator, wherein the tube defines at least an axis; deflection magnets for changing the transmission direction of the ion beam; a collimator for concentrating neutrons; and an irradiation room for receiving a irradiated object, wherein the beam shaping assembly rotates around the axis of the tube.

Implementations of this aspect may include one or more of the following features.

More particularly, the neutron therapy apparatus further includes a supporting frame for holding the beam shaping assembly, the beam shaping assembly rotates around the axis of the tube and/or moves along the supporting frame.

Furthermore, the tube includes a first tube portion defining a first axis and a second tube portion defining a second axis and connected with the first tube portion, the beam shaping assembly rotates around the first axis of the first tube portion or the second axis of the second tube portion.

Furthermore, a first angle is formed between the first tube portion and the second tube portion, the degree of the first angle is changed to adjust the position of the beam shaping assembly relative to the irradiated object in the irradiation room.

Furthermore, the supporting frame includes a first supporting part and a first track set in the first supporting part, the beam shaping assembly is retained on the first track of the supporting frame, the first track is concaved in the supporting frame so as to form a containing room connected with the irradiation room, the collimator extends into the irradiation room through the containing room.

More particularly, both of the first supporting part and the first track are arranged in arc-shape, the first supporting part includes an arc-shaped external surface, the first track is concaved from the arc-shaped external surface of the first supporting part.

More particularly, the tube further includes a third tube portion connected with the neutron generator, a second angle is formed between the second tube portion and the third tube portion, and the degree of the second angle is changed to adjust the position of the beam shaping assembly relative to the irradiated object in the irradiation room.

The deflection magnets are fixed on the supporting frame, the deflection magnets include a first deflection magnet located between the first tube portion and the second tube portion and a second deflection magnet located between the second tube portion and the third tube portion, the ion beam in the first tube portion is transmitted into the second tube portion after the transmission direction is changed by the first deflection magnet, the ion beam in the second tube portion is transmitted into the third tube portion after the transmission direction is changed by the second deflection magnet, the ion beam in the third tube portion irradiates on the neutron generator to generate neutron beams.

More particularly, the supporting frame further includes a second supporting part for supporting the second deflection magnet, the second supporting part includes a second track, the second supporting part moves in the second track while the beam shaping assembly moves in the first track.

The neutron therapy apparatus further includes an accelerator, and the supporting frame further includes a third supporting part, the first deflection magnet is fixed on the third supporting part, the first tube portion is fixed between the accelerator and the first deflection magnet, the third tube portion is connected with the beam shaping assembly and the second deflection magnet, the second tube portion is connected with the first deflection magnet and the second deflection magnet.

In another aspect of the present disclosure, a neutron therapy apparatus is provided to give multi angles neutron beam irradiation, the neutron therapy apparatus includes: a beam shaping assembly including a moderator and a reflector surrounding the moderator, wherein the moderator moderates neutrons to a predetermined energy spectrum and the reflector guides deflected neutrons back to enhance the neutron intensity in the predetermined energy spectrum; a neutron generator embedded inside the beam shaping assembly, wherein the neutron generator generates neutrons after irradiated by an ion beam; at least a tube for transmitting the ion beam to the neutron generator; deflection magnets for changing the transmission direction of the ion beam; a collimator for concentrating neutrons; and a supporting frame, wherein the beam shaping assembly retains on the supporting frame and moves on the supporting part.

More particularly, the supporting frame includes a first supporting part for retaining the beam shaping assembly, a first track is set in the first supporting part, the first track is concaved in the supporting frame to form a containing room which is connected with the irradiation room, the collimator extends into the irradiation room through the containing room.

Furthermore, both of the first supporting part and the first track are arranged in arc-shape, the first supporting part includes an arc-shaped external surface, the first track is concaved from the arc-shaped external surface of the first supporting part.

More particularly, the deflection magnets are fixed on the supporting frame, the deflection magnets include a first deflection magnet and a second deflection magnet, the supporting frame includes a second supporting part having a second track for supporting the second deflection magnet, the second deflection magnet moves in the second track while the beam shaping assembly moves in the first track.

More particularly, the tube includes a first tube portion defining a first axis connected to the accelerator and the first deflection magnet, a third tube portion connected to neutron generator, and a second tube portion defining a second axis connects the first tube portion and the third tube portion, the beam shaping assembly rotates around the first axis or the second axis, the ion beam in the first tube portion is transmitted into the second tube portion after the transmission direction has been changed by the first deflection magnet, the ion beam in the second tube portion is transmitted into the third tube portion after the transmission direction has been changed by the second deflection magnet, the ion beam in the third tube portion irradiates on the neutron generator to generate neutron beams.

Furthermore, the supporting frame further includes a third supporting part, the first deflection magnet is fixed on the third supporting part.

In another aspect of the present disclosure, a neutron therapy apparatus is provided to give multi angles neutron beam irradiation, the neutron therapy apparatus includes: a beam shaping assembly including a moderator and a reflector surrounding the moderator, wherein the moderator moderates neutrons to a predetermined energy spectrum and the reflector guides deflected neutrons back to enhance the neutron intensity in the predetermined energy spectrum; a neutron generator embedded inside the beam shaping assembly, wherein the neutron generator generates neutrons after irradiated by an ion beam; at least two tubes for transmitting the ion beam to the neutron generator; deflection magnets for changing the transmission direction of the ion beam; and a collimator for concentrating neutrons, wherein a first angle is formed between the two tubes, and the degree of the first angle is changeable.

More particularly, the tubes includes a first tube portion connects to the accelerator, a third tube portion connects to the neutron generator, and a second tube portion connects the first portion and the third tube portion, the first angle is formed between the first tube portion and the second tube portion, a second angle is formed between the second tube portion and the third tube portion, at least one of the first angel and the second angel is changeable.

More particularly, the neutron therapy apparatus includes a supporting frame for fixing the deflection magnets, the supporting frame includes a first supporting part with a first track for retaining the beam shaping assembly, the deflection magnets include a first deflection magnet and a second deflection magnet, the supporting frame further includes a second supporting part for supporting the second deflection magnet, the second supporting part includes a second track, the second deflection magnet moves in the second track while the beam shaping assembly moves in the first track.

More particularly, the supporting frame includes a third supporting part, the first deflection magnet is fixed on the third supporting part.

Further areas of applicability will become apparent from the description provided herein. It should be understood that the description and specific examples are intended for purposes of illustration only and are not intended to limit the scope of the present disclosure.

DETAILED DESCRIPTION

The following description of the preferred embodiments is merely exemplary in nature and is in no way intended to limit the invention, its application, or uses.

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components comprise, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^7$Li (p, n) $^7$Be and $^9$Be (p, n) $^9$B and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

BNCT takes advantage that the boron ($^{10}$B)-containing pharmaceuticals have high neutron capture cross section and produces $^4$He and $^7$Li heavy charged particles through $^{10}$B(n,α)$^7$Li neutron capture and nuclear fission reaction. The two charged particles, with average energy at about 2.33 MeV, are of linear energy transfer (LET) and short-range characteristics. LET and range of the alpha particle are 150keV/micrometer and 8 micrometers respectively while those of the heavy charged particle $^7$Li are 175keV/micrometer and 5 micrometers respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

No matter BNCT neutron sources are from the nuclear reactor or the nuclear reactions between the accelerator charged particles and the target, only mixed radiation fields are produced, that is, beams comprise neutrons and photons having energies from low to high. As for BNCT in the depth of tumors, except the epithermal neutrons, the more the residual quantity of radiation ray is, the higher the proportion of nonselective dose deposition in the normal tissue is. Therefore, radiation causing unnecessary dose should be lowered down as much as possible. Besides air beam quality factors, dose is calculated using a human head tissue prosthesis in order to understand dose distribution of the neutrons in the human body. The prosthesis beam quality factors are later used as design reference to the neutron beams, which is elaborated hereinafter.

The International Atomic Energy Agency (IAEA) has given five suggestions on the air beam quality factors for the clinical BNCT neutron sources. The suggestions may be used for differentiating the neutron sources and as reference for selecting neutron production pathways and designing the beam shaping assembly, and are shown as follows:

Epithermal neutron flux >1×10$^9$ n/cm$^2$s
Fast neutron contamination <2×10$^{-13}$ Gy-cm$^2$/n
Photon contamination <2×10$^{-13}$ Gy-cm$^2$/n
Thermal to epithermal neutron flux ratio <0.05
Epithermal neutron current to flux ratio >0.7
Note: the epithermal neutron energy range is between 0.5 eV and 40 keV, the thermal neutron energy range is lower than 0.5 eV, and the fast neutron energy range is higher than 40 keV.

1. Epithermal Neutron Flux

The epithermal neutron flux and the concentration of the boronated pharmaceuticals at the tumor site codetermine clinical therapy time. If the boronated pharmaceuticals at the tumor site are high enough in concentration, the epithermal neutron flux may be reduced. On the contrary, if the concentration of the boronated pharmaceuticals in the tumors is at a low level, it is required that the epithermal neutrons in the high epithermal neutron flux should provide enough doses to the tumors. The given standard on the epithermal neutron flux from IAEA is more than 10$^9$ epithermal neutrons per square centimeter per second. In this flux of neutron beams, therapy time may be approximately controlled shorter than an hour with the boronated pharmaceuticals. Thus, except that patients are well positioned and feel more comfortable in shorter therapy time, and limited residence time of the boronated pharmaceuticals in the tumors may be effectively utilized.

2. Fast Neutron Contamination

Unnecessary dose on the normal tissue produced by fast neutrons are considered as contamination. The dose exhibit positive correlation to neutron energy, hence, the quantity of the fast neutrons in the neutron beams should be reduced to the greatest extent. Dose of the fast neutrons per unit epithermal neutron flux is defined as the fast neutron contamination, and according to IAEA, it is supposed to be less than 2*10$^{-13}$Gy-cm$^2$/n.

3. Photon Contamination (Gamma-ray Contamination)

Gamma-ray long-range penetration radiation will selectively result in dose deposit of all tissues in beam paths, so that lowering the quantity of gamma-ray is further the exclusive requirement in neutron beam design. Gamma-ray dose accompanied per unit epithermal neutron flux is defined as gamma-ray contamination which is suggested being less than 2*10$^{-13}$Gy-cm$^2$/n according to IAEA.

4. Thermal to Epithermal Neutron Flux Ratio

The thermal neutrons are so fast in rate of decay and poor in penetration that they leave most of energy in skin tissue after entering the body. Except for skin tumors like melanocytoma, the thermal neutrons serve as neutron sources of BNCT, in other cases like brain tumors, the quantity of the thermal neutrons has to be lowered. The thermal to epithermal neutron flux ratio is recommended at lower than 0.05 in accordance with IAEA.

5. Epithermal Neutron Current to Flux Ratio

The epithermal neutron current to flux ratio stands for beam direction, the higher the ratio is, the better the forward direction of the neutron beams is, and the neutron beams in the better forward direction may reduce dose surrounding the normal tissue resulted from neutron scattering. In addition, treatable depth as well as positioning posture is improved. The epithermal neutron current to flux ratio is better of larger than 0.7 according to IAEA.

Figure 1:
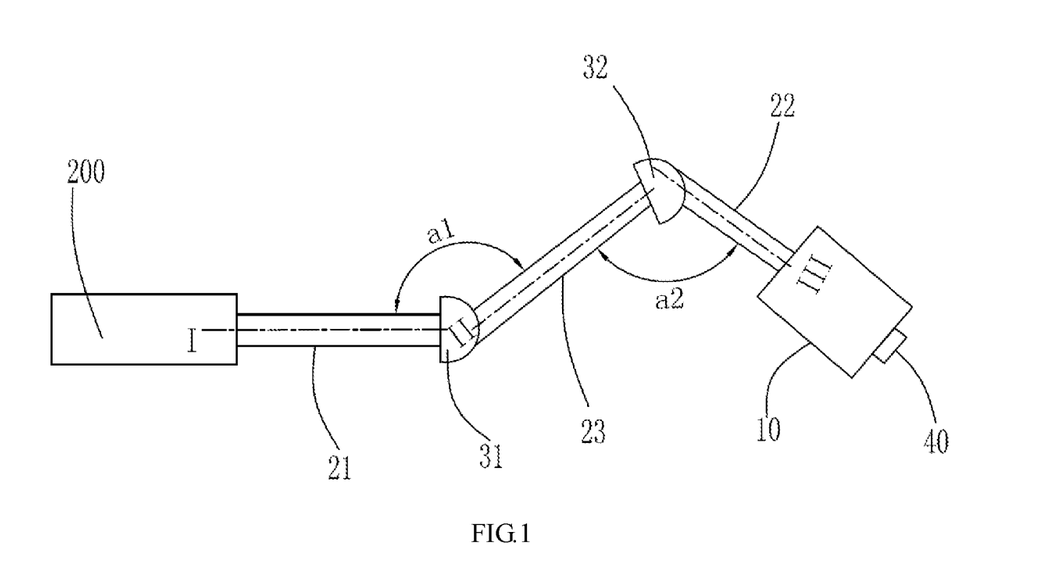
FIG. 1 is a schematic diagram of a neutron therapy apparatus of the present disclosure without a supporting frame.
Figure 2:
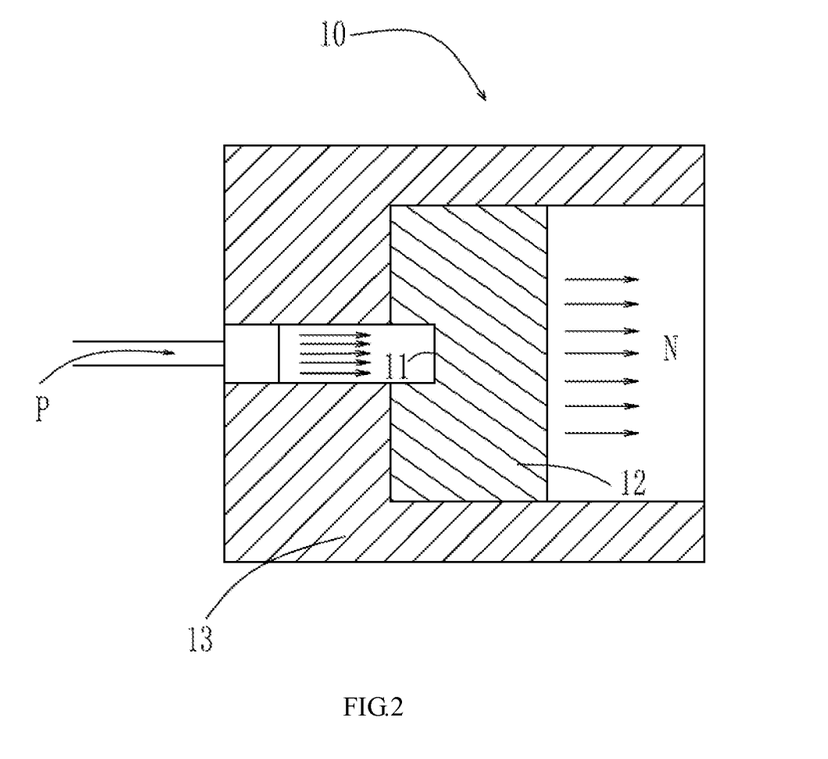
FIG. 2 is a section view of a neutron generator of the present disclosure.

FIG. 1 shows a neutron therapy apparatus 100 of the present application. The neutron therapy apparatus 100 includes a beam shaping assembly 10, a neutron generator 11 which is set inside the beam shaping assembly 10, at least a tube which transmits ion beam P from accelerator 200 to neutron generator 11, and deflection magnets 30 which change the transmission direction of ion beam P in the tube. The beam shaping assembly 10 includes a moderator 12 and a reflector 13 surrounding the moderator 12, the neutron generator 11 is embedded into the moderator 12 (refer to FIG. 2). The beam shaping assembly 10 further includes a beam outlet, and a collimator 40 which is fixed on an end face A where the beam outlet lays in.

Figure 3:
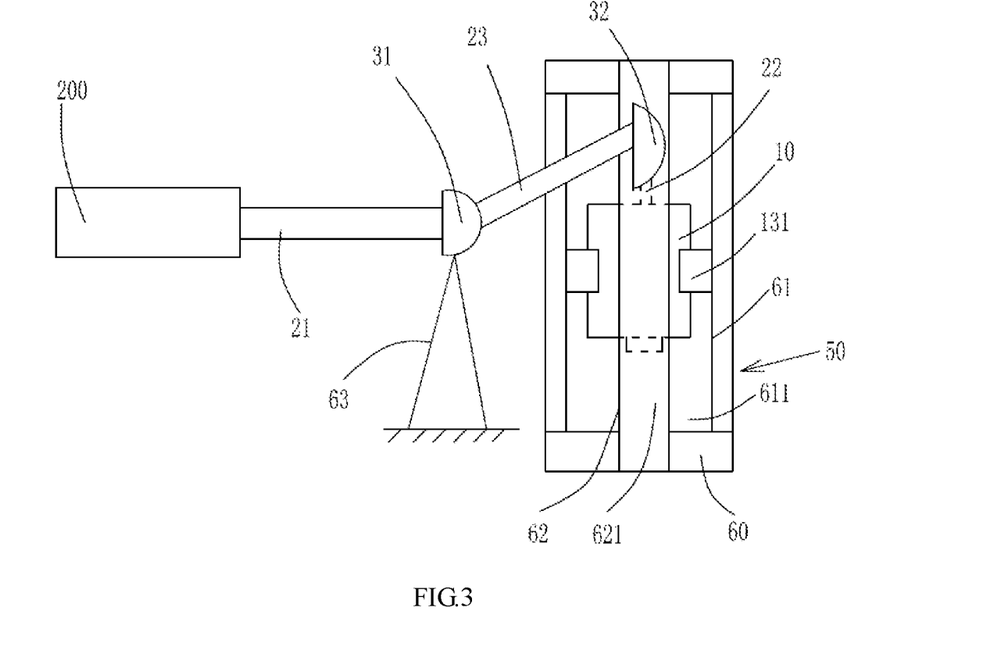
FIG. 3 is a schematic diagram of a neutron therapy apparatus of the present disclosure with a supporting frame.

Referring to FIG. 3, the neutron therapy apparatus 100 further includes an irradiation room 50 for giving irradiation to irradiated object M and a supporting frame 60 for supporting the beam shaping assembly. The supporting frame 60 includes a first supporting part 61. A first track 611 is set in the first supporting part 61. For the convenience of manufacturing, both of the first supporting part 61 and the first track 611 are arc-shaped with the same circle center. In other embodiments, in order to enable the beam shaping assembly to have more irradiation positions in irradiation room 50, the first supporting part 61 and the first track 611 can further be set into other shapes, which are not specifically described herein. The beam shaping assembly 10 is retained on the first track 611 and moves in the first track 611, so that the neutron therapy apparatus can give irradiation to irradiated object M in irradiation room 50 in different angles.

Figure 4:
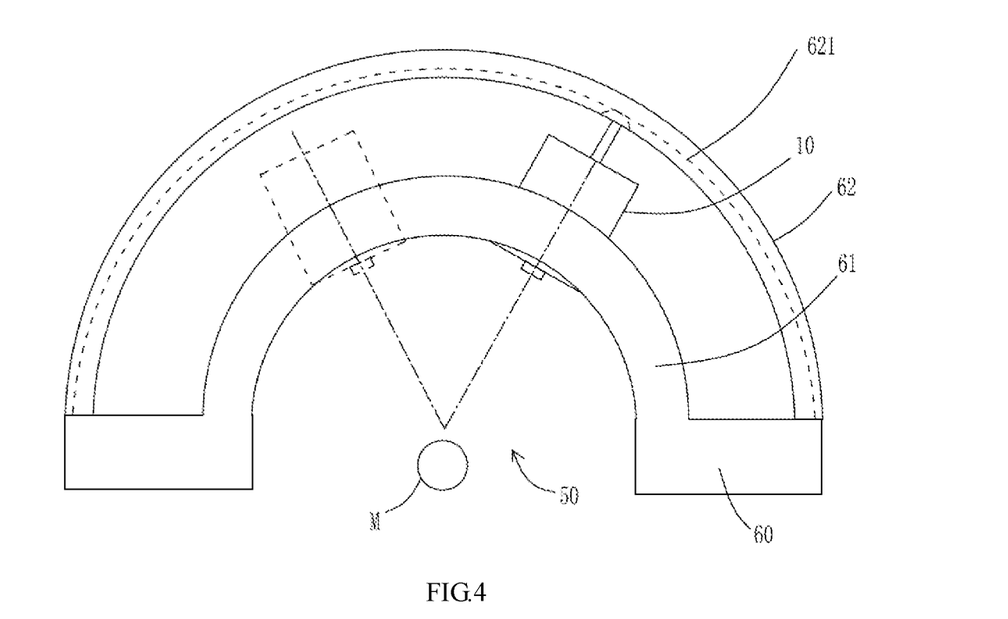
FIG. 4 is a schematic diagram of a beam shaping assembly fixed in the first track in one embodiment of the present disclosure.
Figure 5:
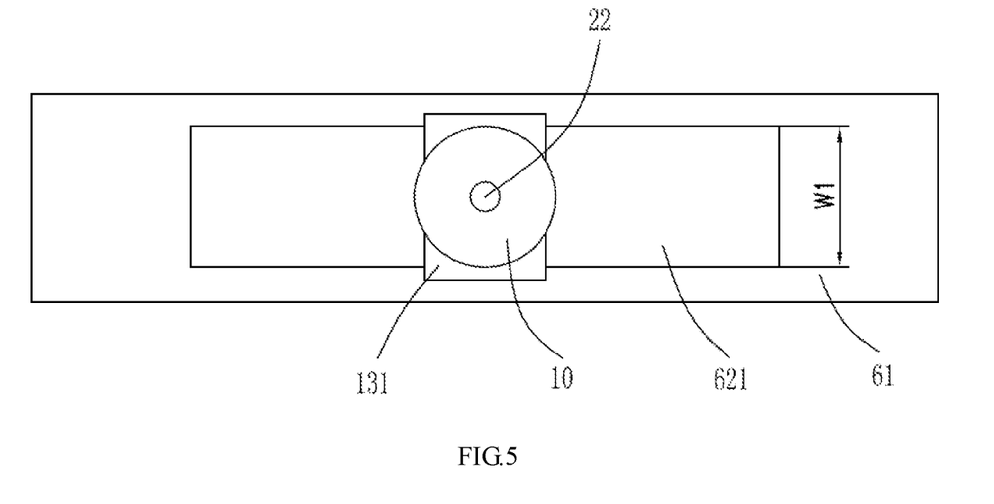
FIG. 5 is a vertical view of a beam shaping assembly fixed in the first track of the supporting part.
Figure 6:
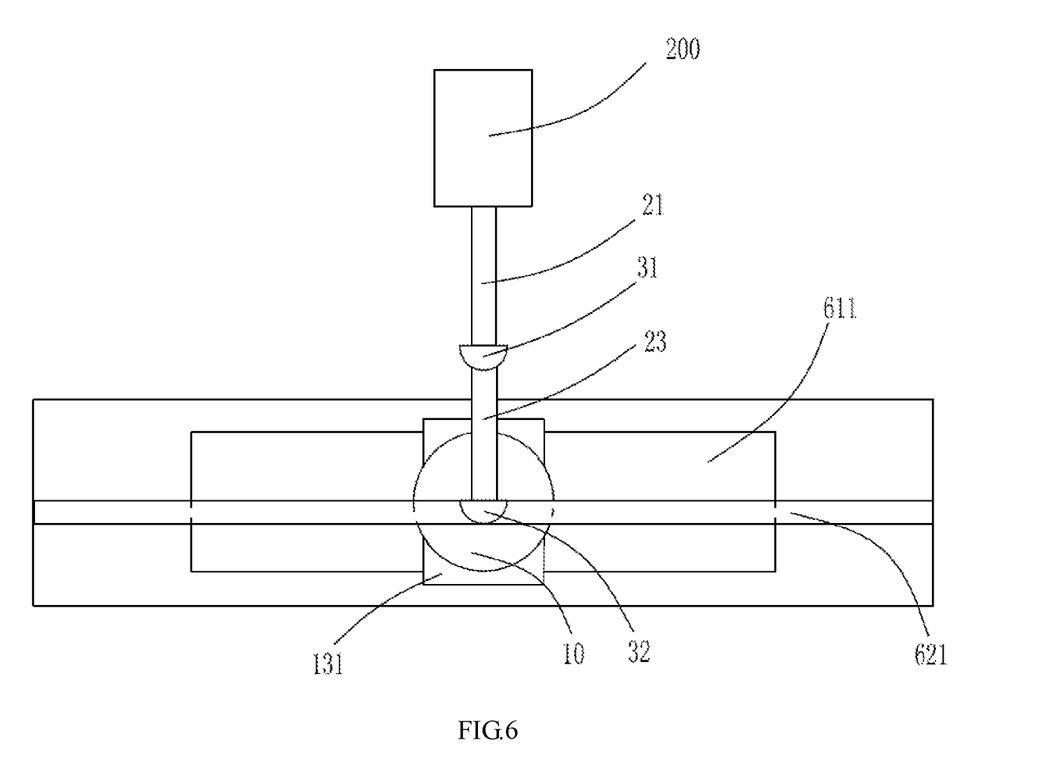
FIG. 6 is a schematic diagram of a neutron therapy apparatus of the present disclosure in another view.

Referring to FIG. 4 to FIG. 6, as one embodiment, the first track 611 is set on the an arc-shaped external surface of the first supporting part 61. The irradiation room 50 is located below the first supporting part 61, the first track 611 is concaved from the arc-shaped external surface of the first supporting part 61, and forms a containing room 612 which is connected with irradiation room 50. A pair of holding protions 131 extend to the two sides of the beam shaping assembly 10 from the external surface of the reflector 13, the holding portions 131 are held by the first track 611 and move in the first track 611, the collimator 40 extends to the irradiation room 50 from the containing room 612. Without doubt, for the miniaturization design of the whole neutron therapy apparatus, holding portions are not necessary, instead, the end face A of the beam shaping assembly equipped with the collimator is coordinated with the first track 611. The end face A is retained on the first track 611 directly, and the neutron therapy apparatus 100 gives multi-angles irradiation to the irradiated object M by the movement of end face A in the first track 611.

As another embodiment, the irradiation room 50 is located at one side of the first supporting part 61 instead of setting below the first supporting part 61, a holding portion extends out from the beam shaping assembly 10 and is located at one side of the beam shaping assembly 10, the holding portion is retained in the first track 611 and moves in the first track 611. The beam outlet of the beam shaping assembly 10 is facing to the irradiation room 50, so that the neutron therapy apparatus 100 can irradiate the irradiated object M (unshown in the Figures) in different angles as the beam shaping assembly 10 moves in the first track 611.

The first track can further be set in a front face of the first supporting part. The holding portions extend out from the external surface of the reflector and is located at one side of the beam shaping assembly, the holding portions are held in the first track and move in the first track. There are many other emplements, for example, the beam shaping assembly is retained in the first track 611 by part of the reflector without setting holding portions, as long as the reflector is able to move in the first track and the neutron therapy apparatus is able to irradiate object M in irradiation room in different angles, which are not introduced in detail herein.

The tube includes a first tube portion 21 fixed on accelerator 200, a third tube portion 22 fixed on neutron generator 11 and a second tube portion 23 connects the first tube portion 21 and the third tube portion 22. The first tube portion 21 defines a first axis I and the second tube portion 23 defines a second axis II. The deflection magnet 30 includes a first deflection magnet 31 and a second deflection magnet 32. One end of the first tube portion 21 is connected to accelerator 200, the other end is connected to the first deflection magnet 31; one end of the second tube portion 23 is connected to the first deflection magnet 31, the other end is connected to the second deflection magnet 32; one end of the third tube portion 22 is connected to the second deflection magnet 32, and the other end is connected to the beam shaping assembly 10. The beam shaping assembly 10 is able to rotate around the first axis I of the first tube portion 21 or the second axis II of the second tube portion 23, to change the irradiation angles of the beam shaping assembly 10. The transmission direction of ion beam P in the first tube portion 21 is deflected by the first deflection magnet 31 and transmitted into the second tube portion 23, after being deflected by the second deflection magnet 32, the ion beams P in the second tube portion 23 are transmitted into the third tube portion 22, the ion beams P in the third tube portion 22 are transmitted to the neutron generator 11 to generate neutron beams, the neutron beams are applied to the irradiation of neutron therapy apparatus 100.

Figure 9:
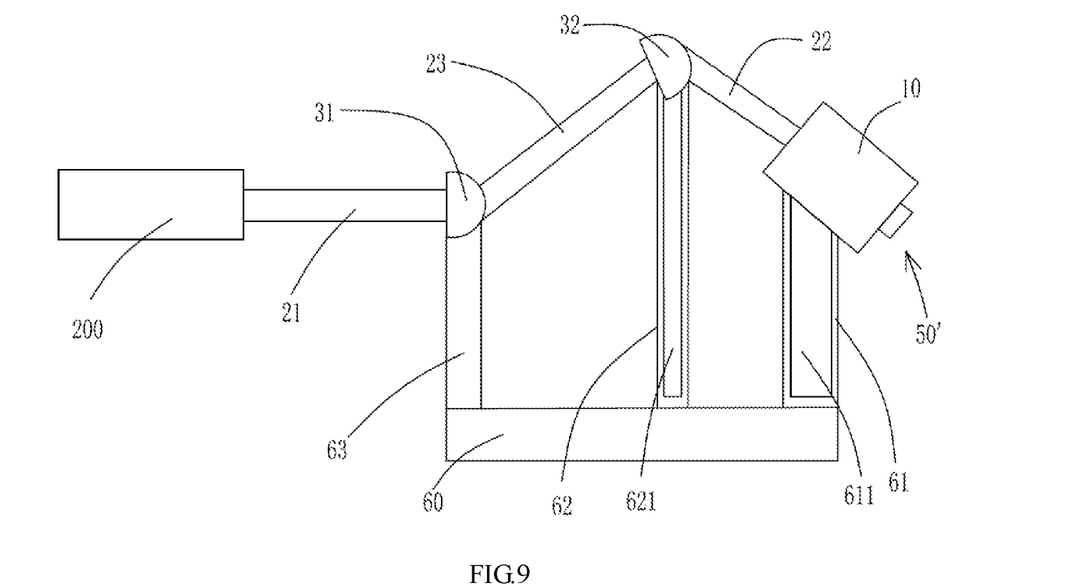
FIG. 9 is a schematic diagram of another embodiment of the supporting frame of the present disclosure.

The supporting frame 60 further includes a second supporting part 62 above the first supporting part 61, the second deflection magnet 32 is retained on the second supporting part 62, a second track 621 is set in the second supporting part 62 to allow the second deflection magnet 32 to move in the second track 621 along with the beam shaping assembly 10. The concrete structure of the second track 621 can refer to that of the first track 611 mentioned foregoing, which is used for the retaining of the beam shaping assembly 10 and allows the movement of beam shaping assembly 10. The second supporting part 62 can further be set behind the first supporting part 61, as shown in FIG. 9.

The beam shaping assembly 10 moves in the first track 611 according to different irradiation angles needed by the irradiated object M, when the beam shaping assembly 10 moves in the first track 611 and rotates around the first axis I, the third tube portion 22 moves along with the beam shaping assembly 10, and the second deflection magnet 32 moves in the second track 621 along with the movement of the third tube portion 22, the multi-angles irradiation of the neutron therapy apparatus 100 give to the irradiated object M in the irradiation room 50 is achieved. Without doubt, the beam shaping assembly 10 can further be set into a structure that can rotate around the second axis II of the second tube portion 23 to realize the multi-angles irradiation to the irradiated object in irradiation room 50, which is not elaborated here.

Figure 7:
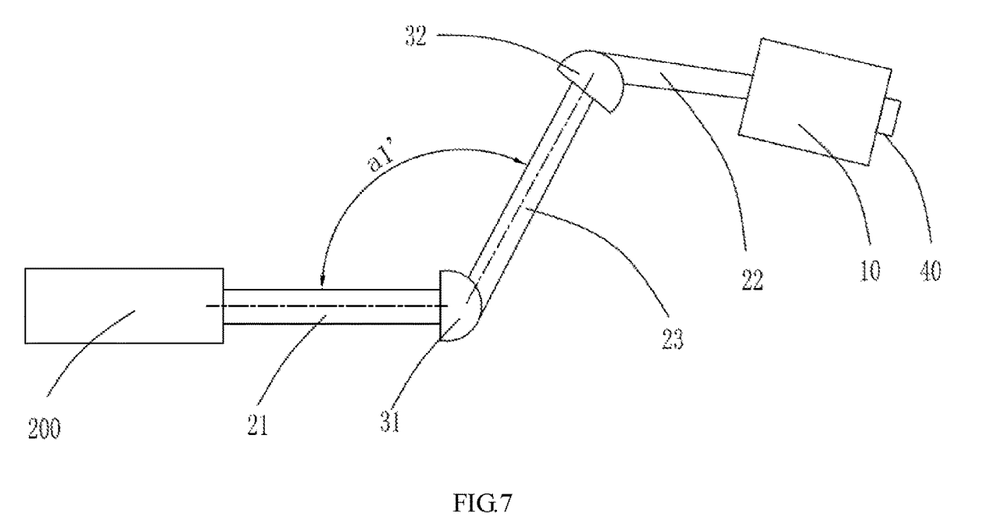
FIG. 7 is a schematic diagram of a neutron therapy apparatus of the present disclosure, wherein the first angle a1 is changed.
Figure 8:
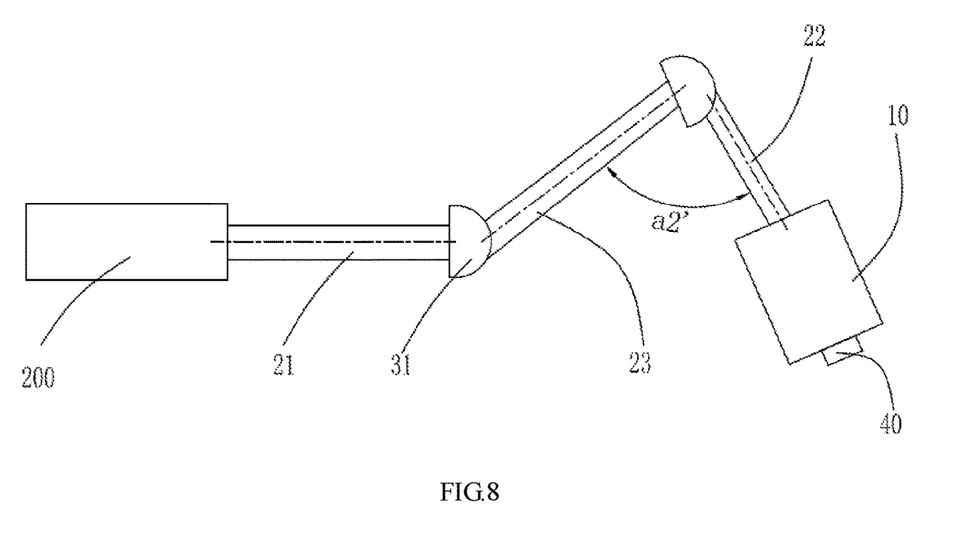
FIG. 8 is a schematic diagram of a neutron therapy apparatus of the present disclosure, wherein the second angle a2 is changed.

As shown in FIG. 7 and FIG. 8, a first angle a1 is formed between the first tube portion 21 and the second tube portion 23, and a second angle a2 is formed between the second tube portion 23 and the third tube portion 22, the degree of both the first angle a1 and the second angle a2 can be changed. According to actual requirement, at least one of the first angle a1 and second angle a2 or both of the first angle and the second angle can be set to be changed, to reduce the limitation of the irradiation angle of beam shaping assembly 10.

The neutron therapy apparatus 100 further includes a third supporting part 63 which is used for retaining the first deflection magnet 31. The third supporting part 63 can be retained on the supporting frame 60, as shown in FIG. 9, and it can further be directly fixed on the ground, as shown in FIG. 3.

The following is the detailed description to the whole rotation process of the neutron therapy apparatus.

Firstly, determine a irradiation direction according to the specific situations of the irradiated object. According to the determined irradiation direction, the beam shaping assembly 10 moves in the first track 611 to a position that can give irradiation to the irradiated object from such an angle, then position the third tube portion 22 after it moves to some specific place along with the beam shaping assembly 10.

Secondly, determine the deflecting directions of the first deflection magnet 31 and the second deflection magnet 32 according to the position of the first tube portion 21, the third tube portion 22 and the second tube portion 23. For the position of the first tube portion 21 has been fixed, the position of the third tube portion 22 is determined by the movement of the beam shaping assembly 10. The second tube portion 23 is located between the first tube portion 21 and the third tube portion 22, the first deflection magnet 31 and the second deflection magnet 32 are fixed on each end of the second tube portion 23 respectively. Therefore the position of the second tube portion 23 can be at any position that can be acquired in the space after the positions of the first tube portion 21 and the third tube portion 22 have been determined. The deflecting directions of the first deflection magnet 31 and the second deflection magnet 32 are determined by the positions of the three tube portions, so that ion beam P can be transmitted into neutron generator 11 from accelerator 200.

The ion beam P in the first tube portion 21 is transmitted into the second tube portion 23 after the transmission direction has been changed by the first deflection magnet 31. And then the ion beam P in the second tube portion 23 is transmitted into the third tube portion 22 after the transmission direction has been changed by the second deflection magnet 32. The ion beam P in the third tube portion 22 is directly irradiated to the neutron generator 11 to generate neutron beams, and the neutron beams give irradiation to the irradiated object.

What should be pointed out is that, although the beam shaping assembly described above has the capability of shielding radioactive rays, extra shielding assembly can provide better shielding effect in the process of irradiation therapy for the irradiated object. Especially when the first track 611 is concaved from the external surface of the first supporting part 61 and forms a containing room 612 connects with the irradiation room 50 (refer to FIG. 5), a gap is formed between the beam shaping assembly 10, the containing room 612 and the irradiation room 50. In one aspect, such a gap will affect the aesthetics of the whole neutron therapy apparatus, in another aspect, such a gap will increase the leakage of radioactive rays in the process of irradiation. Therefore a shielding assembly 70 (70') is necessary to cover the containing room 612 and shields the irradiation room 50 in the process of irradiation.

Combined with the Figures, the specific structure of shielding assembly 70 (70') is illustrated in the following. The shielding assembly 70 (70') is able to move along with the movement of the beam shaping assembly 10 and shield the leakage of radioactive rays from the irradiation room 50.

Figure 10:
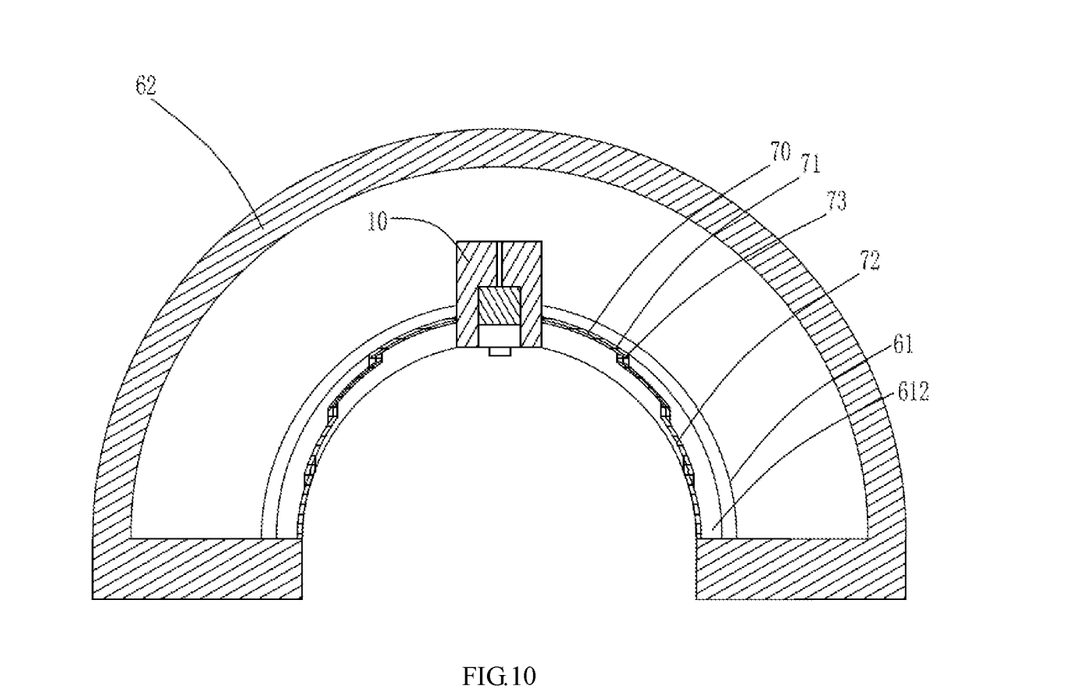
FIG. 10 is a section view of a shielding assembly in one embodiment of the present disclosure.
Figure 11:
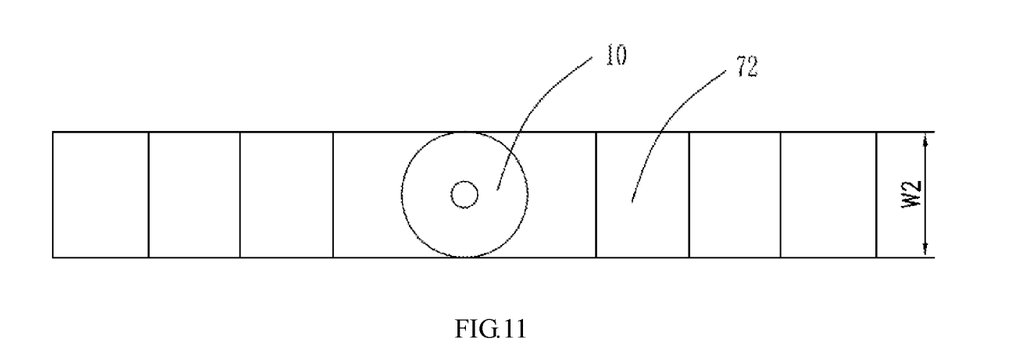
FIG. 11 is a state diagram of shielding parts of the present disclosure, wherein the beam shaping assembly locates at a first position in the first track.
Figure 12:
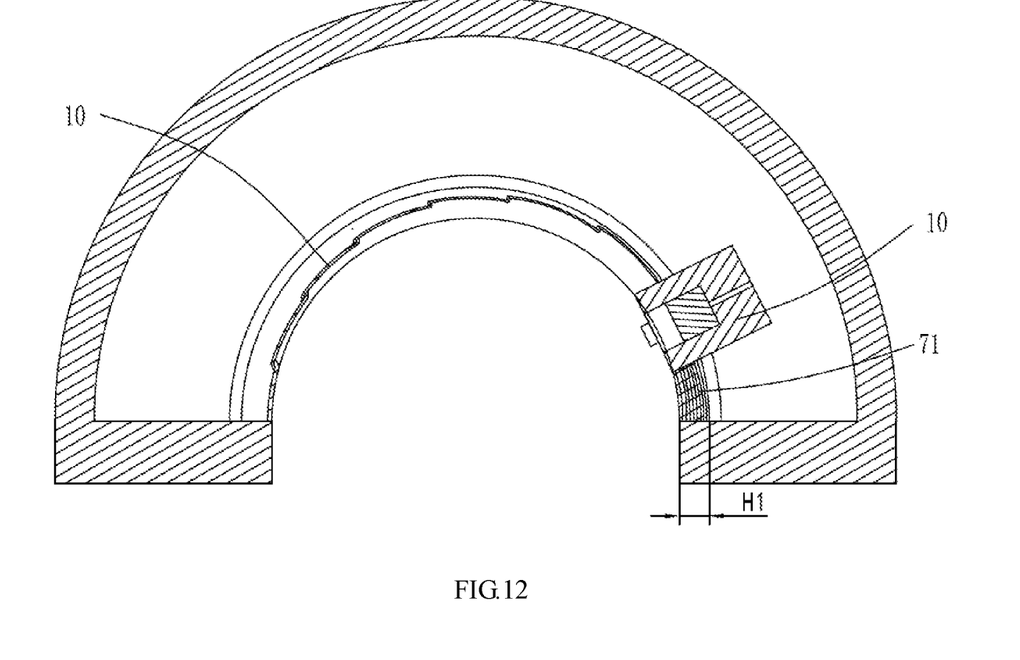
FIG. 12 is a state diagram of shielding parts of the present disclosure, wherein the beam shaping assembly locates at a second position in the first track.

Referring to FIG. 10 and FIG. 11, the shielding assembly 70 includes two shielding parts 71 which can stretch out or contract along with the moving direction of the beam shaping assembly 10. The shielding parts 71 are located on two sides of the beam shaping assembly 10 respectively, one end of the shielding part 71 is connected with the supporting frame 60 and the other end is connected with the beam shaping assembly 10.

Each shielding part 71 includes multi shielding portions 72 whose heads and tails are buckled on each other. A locking portion 73 is set on each end of the shielding portion 72. The locking portion 73 is able to move on the surface of the shielding portion 72 and mutually buckled on the locking portion adjoined to it. When the shielding part 71 contracts, the shielding portions 72 stack together one by one; when the shielding part 71 stretches out, the shielding portions 72 expand out one by one and buckled on each other, therefore the two adjoining shielding portions 72 are positioned. If part of the shielding part 71 stretches out, that is, as shown in FIG. 10, some shielding portions 72 are expanding out, while some others still are stacked together. In conclusion, due to the movement of the beam shaping assembly 10, the shielding portions 72 expand out or stack together.

Figure 13:
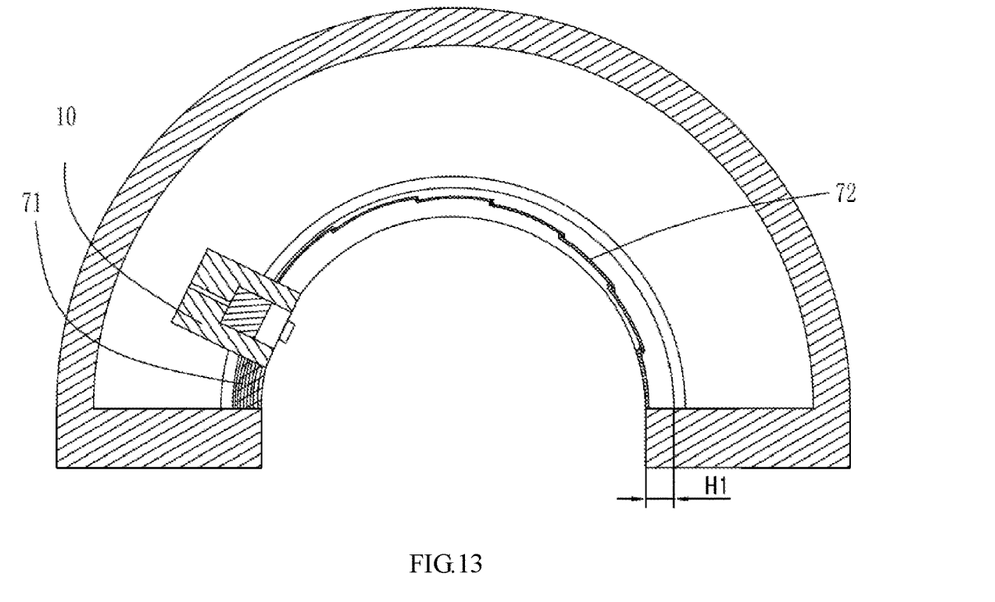
FIG. 13 is a vertical view of shielding assembly of the present disclosure.
Figure 14:
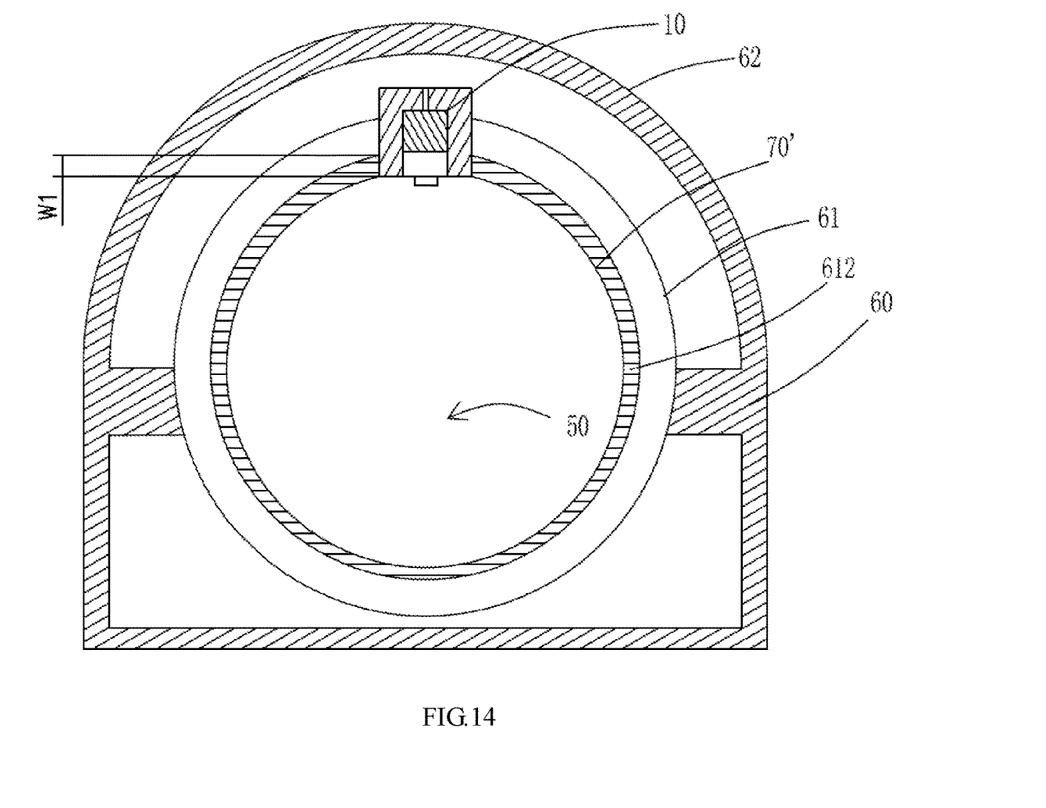
FIG. 14 is a section view of shielding assembly in a second embodiment of the present disclosure.

As shown in FIG. 13 and FIG. 14, when the beam shaping assembly 10 moves along the first supporting frame 61, the shielding part 71 located at one side of the beam shaping assembly 10 contracts and the shielding portions on this side gradually stack, and the shielding part 71 located at the other side of the beam shaping assembly 10 stretches out and the shielding portions on this side gradually expand out. When the shielding portions 72 stack together, the shielding part 71 far away from the irradiation room 50 is connected to the beam shaping assembly 10, and the portion of the shielding part 71 close to the irradiation room 50 is connected to the supporting frame 60.

As described above, the first track 611 is set in arc-shape. In this embodiment, in order to achieve better shielding effect, every shielding portion 72 is set in arc-shape. After the shielding portions 72 stretch out one by one, the whole shielding part 71 is in arc-shape.

In order to masximumly reduce the leakage of radioactive rays in the process of irradiation, the height H1 of the containing room 612 is not less than the thickness of the shielding assembly 70, the thickness of the shielding assembly 70 refers to the thickness of the multi shielding portions 72 stacked together. And the width W2 of the shielding assembly 70 is not less than the width W1 of the containing room 612.

Figure 15:
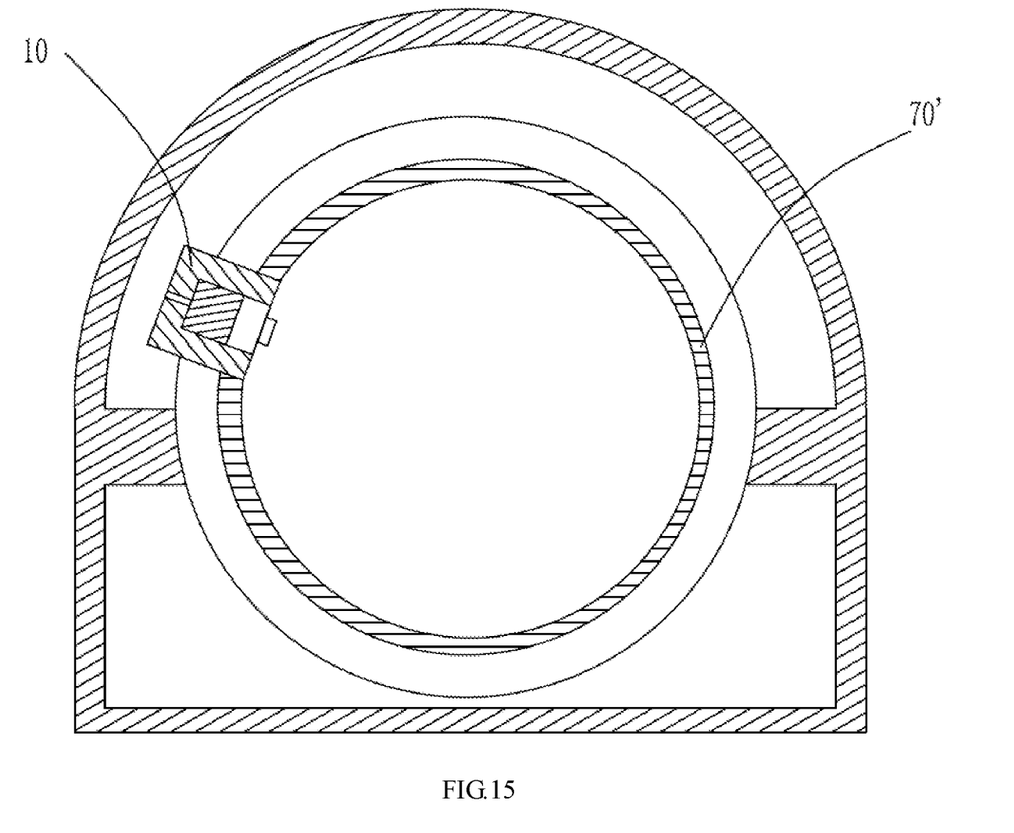
FIG. 15 is a state diagram of shielding assembly of the present disclosure wherein the beam shaping assembly locates at a certain position.
Figure 16:
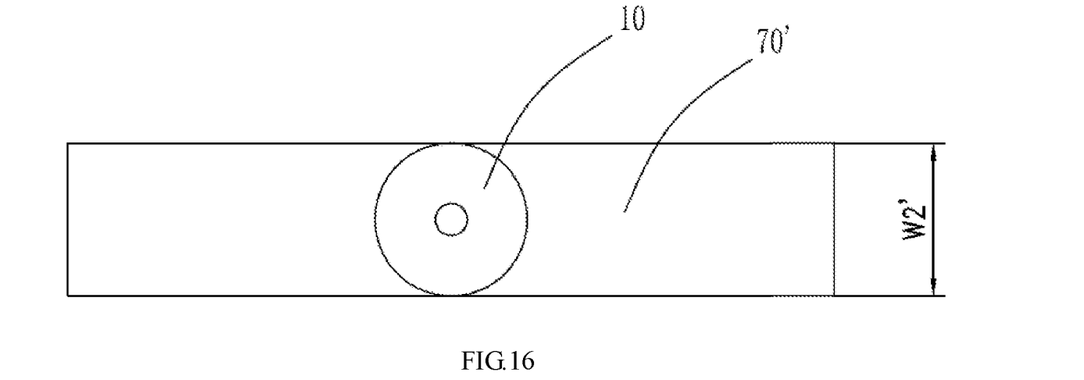
FIG. 16 is a vertical view of shielding assembly shown in FIG. 10.

FIG. 15 shows another embodiment of shielding assembly 70'. The shielding assembly 70' is connected to both sides of the beam shaping assembly 10 and forms the irradiation room 50 described before. The shielding assembly 70' is an integal structure and is able to rotate around the supporting frame 61 along with the movement of the beam shaping assembly 10 (as shown in FIG. 16), and is able to shield the radioactive rays leaking from the irradiation room 50. In this embodiment, the shielding assembly 70' is contained in the containing room 612, and the width W2' of the shielding assembly 70' is not less than the width W1 of the containing room 612. Without doubt, the thickness of the shielding assembly 70' can further be set to be not more than the height H1 of the containing room 612.

In one aspect, the shielding assembly 70 (70') can shield the radioactive rays leaked from the beam shaping assembly 10, in another aspect, it covers in the gap formed between the irradiation room 50, containing room 612 and the beam shaping assembly 10, which is benefit to its aesthetics.

In addition, a shielding wall (not labeled) can further be set at the outer side of the shielding assembly, which is able to move away from or close to the shielding assembly 10 and is able to support the shielding assembly. When the shielding wall moves away from the shielding assembly, the beam shaping assembly 10 rotates on the supporting frame 60 according to actual requirement, to get a proper irradiation position, and the shielding assembly moves along with the movement of the beam shaping assembly 10 and covers the irradiation room 50 and shields the radioactive rays all the time; when the beam shaping assembly 10 is located at the proper irradiation position, the shielding wall moves close to the shielding assembly and the shielding assembly is supported by the shielding assembly, the beam shaping assembly 10 irradiates to the irradiation room 50, and the shielding assembly shields the irradiation room 50.

In one aspect, the setting of the shielding wall provides a supporting force for the shielding assembly, and shares part of the supporting force the supporting frame suffered; in another aspect, it shields the radioactive rays generated in the process of irradiation and increases the shielding effect.

The arc-shape described herein indicates not only a certain arc-shape on a circle, but also the shapes formed by the connection of multi sections of straight lines, regular or irregular curves, which are similar to the arc-shape, all belong to the arc-shape described in the application.

It should be understood that, the terms used herein such as "having", "comprise" and "include" do not exclude the existence or addition of one or more other components or the combinations thereof.

The above illustrates and describes basic principles, main features and advantages of the present disclosure. Those skilled in the art should appreciate that the above embodiments do not limit the present disclosure in any form. Technical solutions obtained by equivalent substitution or equivalent variations all fall within the scope of the present disclosure.

The invention claimed is:

1. A neutron therapy apparatus, comprising:
   a beam shaping assembly including a moderator and a reflector surrounding the moderator, wherein the moderator moderates neutrons to a predetermined energy spectrum and the reflector guides deflected neutrons back to enhance the neutron intensity in the predetermined energy spectrum;
   a neutron generator embedded inside the beam shaping assembly, wherein the neutron generator generates neutrons after irradiated by an ion beam;
   at least a tube for transmitting the ion beam to the neutron generator, wherein the tube defines at least an axis, the tube comprises a first tube portion defining a first axis and a second tube portion defining a second axis and connected with the first tube portion, the beam shaping assembly rotates around the first axis of the first tube portion or the second axis of the second tube portion;
   deflection magnets for changing the transmission direction of the ion beam;
   a collimator for concentrating neutrons;
   a supporting frame for holding the beam shaping assembly, wherein the supporting frame comprises a first supporting part and a first track set in the first supporting part, and the beam shaping assembly is retained on the first track of the supporting frame; and
   an irradiation room for receiving a irradiated object, wherein the first track is recessed in the supporting frame so as to form a containing room connected with the irradiation room, and the collimator extends into the irradiation room through the containing room,
   wherein the beam shaping assembly rotates around the axis of the tube and/or moves along the supporting frame.

2. The neutron therapy apparatus according to claim 1, wherein a first angle is formed between the first tube portion and the second tube portion, the degree of the first angle is changed to adjust the position of the beam shaping assembly relative to the irradiated object in the irradiation room.

3. The neutron therapy apparatus according to claim 1, wherein both of the first supporting part and the first track are arranged in arc-shape, the first supporting part includes an arc-shaped external surface, the first track is recessed from the arc-shaped external surface of the first supporting part.

4. The neutron therapy apparatus according to claim 1, wherein the tube further comprises a third tube portion connected with the neutron generator, a second angle is formed between the second tube portion and the third tube portion, and the degree of the second angle is changed to adjust the position of the beam shaping assembly relative to the irradiated object in the irradiation room.

5. The neutron therapy apparatus according to claim 4, wherein the deflection magnets are fixed on the supporting frame, the deflection magnets comprise a first deflection magnet located between the first tube portion and the second tube portion and a second deflection magnet located between the second tube portion and the third tube portion, the ion beam in the first tube portion is transmitted into the second tube portion after the transmission direction is changed by the first deflection magnet, the ion beam in the second tube portion is transmitted into the third tube portion after the transmission direction is changed by the second deflection magnet, the ion beam in the third tube portion irradiates on the neutron generator to generate neutron beams.

6. The neutron therapy apparatus according to claim 5, wherein the supporting frame further comprises a second supporting part for supporting the second deflection magnet, the second supporting part comprises a second track, the second supporting part moves in the second track while the beam shaping assembly moves in the first track.

7. The neutron therapy apparatus according to claim 5, wherein the neutron therapy apparatus further comprises an accelerator, and the supporting frame further comprises a third supporting part, the first deflection magnet is fixed on the third supporting part, the first tube portion is fixed between the accelerator and the first deflection magnet, the third tube portion is connected with the beam shaping assembly and the second deflection magnet, the second tube portion is connected with the first deflection magnet and the second deflection magnet.

8. A neutron therapy apparatus, comprising:
   a beam shaping assembly including a moderator and a reflector surrounding the moderator, wherein the moderator moderates neutrons to a predetermined energy spectrum and the reflector guides deflected neutrons back to enhance the neutron intensity in the predetermined energy spectrum;
   a neutron generator embedded inside the beam shaping assembly, wherein the neutron generator generates neutrons after irradiated by an ion beam;
   at least a tube for transmitting the ion beam to the neutron generator;
   deflection magnets for changing the transmission direction of the ion beam;
   a collimator for concentrating neutrons; and
   a supporting frame, wherein the supporting frame comprises a first supporting part for retaining the beam shaping assembly, a first track is set in the first supporting part, the first track is recessed in the supporting frame to form a containing room which is connected with the irradiation room, and the collimator extends into the irradiation room through the containing room, wherein the beam shaping assembly retains on the supporting frame and moves on the supporting frame.

9. The neutron therapy apparatus according to claim 8, wherein both of the first supporting part and the first track are arranged in arc-shape, the first supporting part includes an arc-shaped external surface, the first track is recessed from the arc-shaped external surface of the first supporting part.

10. The neutron therapy apparatus according to claim 8, wherein the deflection magnets are fixed on the supporting frame, the deflection magnets comprise a first deflection magnet and a second deflection magnet, the supporting frame comprises a second supporting part having a second track for supporting the second deflection magnet, the second deflection magnet moves in the second track while the beam shaping assembly moves in the first track.

11. The neutron therapy apparatus according to claim 10, wherein the tube comprises a first tube portion defining a first axis connected to the accelerator and the first deflection magnet, a third tube portion connected to neutron generator, and a second tube portion defining a second axis connects the first tube portion and the third tube portion, the beam shaping assembly rotates around the first axis or the second axis, the ion beam in the first tube portion is transmitted into the second tube portion after the transmission direction has been changed by the first deflection magnet, the ion beam in the second tube portion is transmitted into the third tube portion after the transmission direction has been changed by the second deflection magnet, the ion beam in the third tube portion irradiates on the neutron generator to generate neutron beams.

12. The neutron therapy apparatus according to claim 11, wherein the supporting frame further comprises a third supporting part, the first deflection magnet is fixed on the third supporting part.

13. A neutron therapy apparatus, comprising:
a beam shaping assembly including a moderator and a reflector surrounding the moderator, wherein the moderator moderates neutrons to a predetermined energy spectrum and the reflector guides deflected neutrons back to enhance the neutron intensity in the predetermined energy spectrum;
a neutron generator embedded inside the beam shaping assembly, wherein the neutron generator generates neutrons after irradiated by an ion beam;
at least two tubes for transmitting the ion beam to the neutron generator;
deflection magnets for changing the transmission direction of the ion beam, wherein the deflection magnets comprise a first deflection magnet and a second deflection magnet;
a collimator for concentrating neutrons; and
a supporting frame for fixing the deflection magnets, wherein the supporting frame comprises a first supporting part with a first track for retaining the beam shaping assembly and a second supporting part for supporting the second deflection magnet, the second supporting part comprises a second track, and the second deflection magnet moves in the second track while the beam shaping assembly moves in the first track,
wherein a first angle is formed between the two tubes, and the degree of the first angle is changeable.

14. The neutron therapy apparatus according to claim 13, wherein the tubes comprises a first tube portion connects to the accelerator, a third tube portion connects to the neutron generator, and a second tube portion connects the first portion and the third tube portion, the first angle is formed between the first tube portion and the second tube portion, a second angle is formed between the second tube portion and the third tube portion, at least one of the first angel and the second angel is changeable.

15. The neutron therapy apparatus according to claim 13, wherein the supporting frame comprises a third supporting part, the first deflection magnet is fixed on the third supporting part.

* * * * *